US00PP13788P29

(12) United States Plant Patent
Bartels

(10) Patent No.: US PP13,788 P2
(45) Date of Patent: May 6, 2003

(54) ROSE PLANT NAMED 'ROROONE'

(75) Inventor: Gosen B. H. Bartels, Aalsmeer (NL)

(73) Assignee: Bartels Roses BV, Aalsmeer (NL)

( * ) Notice: Subject to any disclaimer, the term of this patent is extended or adjusted under 35 U.S.C. 154(b) by 0 days.

(21) Appl. No.: 10/036,939

(22) Filed: Dec. 31, 2001

(51) Int. Cl.[7] ..... A01H 5/00
(52) U.S. Cl. ..... Plt./133
(58) Field of Search ..... Plt./133

(56) References Cited

U.S. PATENT DOCUMENTS

PP11,184 P * 1/2000 Delbard ..... Plt./133

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Rose plant named 'Roroone', characterized by its erect flowering stems with relatively few thorns; shiny dark green leaves; creamy white-colored flowers; fragrant flowers; and good postproduction longevity.

1 Drawing Sheet

BOTANICAL CLASSIFICATION/CULTIVAR DESIGNATION

*Rosa hybrida* cultivar Roroone.

BACKGROUND OF THE INVENTION

The present Invention relates to a new and distinct cultivar of Rose plant, botanically known as *Rosa hybrida*, commercially used as a hybrid tea cut Rose, and hereinafter referred to by the name 'Roroone'.

The new Rose is a product of a planned breeding program conducted by the Inventor in Aalsmeer, The Netherlands. The objective of the breeding program was to develop new cut Rose cultivars with large flowers with attractive color and good postproduction longevity.

The new Rose originated from a cross made by the Inventor in Aalsmeer, The Netherlands of the *Rosa hybrida* cultivar Tineke, disclosed in U.S. Plant Pat. No. 8,055, as the female, or seed, parent and the *Rosa hybrida* cultivar Sandy Femma, not patented, as the male, or pollen, parent. The new Rose was discovered and selected by the Inventor in 1998 as a flowering plant within the progeny of the stated cross in a controlled environment in Aalsmeer, The Netherlands. The selection of this new Rose was based on its large flowers and attractive flower color.

Asexual reproduction of the new cultivar by cuttings taken in a controlled environment in Aalsmeer, The Netherlands since 1998, has shown that the unique features of this new Rose are stable and reproduced true to type in successive generations of asexual propagation.

SUMMARY OF THE INVENTION

Plants of the cultivar Roroone have not been observed under all possible environmental conditions. The phenotype may vary somewhat with variations in environment such as temperature and light intensity without, however, any variance in genotype.

The following traits have been repeatedly observed and are determined to be the unique characteristics of 'Roroone'. These characteristics in combination distinguish 'Roroone' as a new and distinct cultivar:

1. Erect flowering stems with relatively few thorns.
2. Shiny dark green leaves.
3. Creamy white-colored flowers; outer petals overlain with green.
4. Fragrant flowers.
5. Good postproduction longevity.

Plants of the new Rose differ primarily from plants of the male parent, the cultivar Sandy Femma, in the following characteristics:

1. Plants of the new Rose have larger flowers than plants of the cultivar Sandy Femma.
2. Flowers of plants of the new Rose and the cultivar Sandy Femma differ in flower color as plants of the cultivar Sandy Femma have light yellow brown-colored flowers.

Plants of the new Rose are similar to plants of the female parent, the cultivar Tineke. In side-by-side comparisons conducted in Aalsmeer, The Netherlands, plants of the new Rose differed from plants of the cultivar Tineke in the following characteristics:

1. Plants of the new Rose had shorter flowering stems than plants of the cultivar Tineke.
2. Flowering stems of plants of the new Rose had fewer thorns than flowering stems of plants of the cultivar Tineke.
3. Plants of the new Rose were more vigorous and produced flowering stems about two weeks earlier than plants of the cultivar Tineke.
4. Plants of the new Rose had smaller flowers than plants of the cultivar Tineke.
5. Flowers of plants of the new Rose were fragrant whereas flowers of plants of the cultivar Tineke were not fragrant.
6. Flowering stems of plants of the new Rose had better postproduction longevity than flowering stems of the cultivar Tineke.

BRIEF DESCRIPTION OF THE PHOTOGRAPH

The accompanying colored photograph illustrates the overall appearance of the new Rose, showing the colors as true as it is reasonably possible to obtain in colored reproductions of this type. Colors in the photograph may differ slightly from the color values cited in the detailed botanical description which accurately describe the colors of the new Rose. The photograph comprises a side perspective view of four typical flowering stems of 'Roroone'.

DETAILED BOTANICAL DESCRIPTION

The aforementioned photographs, following observations, measurements and values describe plants of the new Rose grown in Aalsmeer, The Netherlands in a glass-covered greenhouse in 12-liter containers. During the production of the plants, day temperatures averaged 21° C., night temperatures averaged 19° C., and light levels averaged 6,000 lux. Plants used for the photograph and description were about 7 months from planting rooted young plants.

Color references are made to The Royal Horticultural Society Colour Chart, 1995 Edition, except where general terms of ordinary dictionary significance are used.

Botanical classification: *Rosa hybrida* cultivar Roroone.

Parentage:

*Female parent.*—*Rosa hybrida* cultivar Tineke, disclosed in U.S. Plant Pat. No. 8,055.

*Male parent.*—*Rosa hybrida* cultivar Sandy Femma, not patented.

Propagation:

*Type.*—By cuttings.

*Time to initiate roots.*—Summer: About 14 days at 25° C. Winter: About 21 days at 25° C.

*Time to produce a rooted young plant.*—Summer: About 25 days at 23° C. Winter: About 30 days at 23° C.

*Root description.*—Fibrous.

*Rooting habit.*—Freely branching.

Plant description:

*Plant habit.*—Narrowly upright, columnar.

*Time from planting to harvest.*—Fast, about 7 weeks.

*Flowering stem (peduncle) description.*—Quantity: About two flowering stems per plant at one time. Aspect: Erect. Length: About 60 to 80 cm. Spread: About 50 cm. Diameter: About 5 mm. Strength: Strong. Texture: Smooth, glabrous; relatively few red-colored thorns, 60A in color. Color: 138A.

*Foliage description.*—Leaves compound with three to five leaflets; alternate, generally symmetrical, durable and long persisting. Quantity of leaves per flowering stem: About 8 to 10. Length: Entire compound leaf: About 16 cm. Terminal leaflet: About 5 cm. Width: Entire compound leaf: About 11 cm. Terminal leaflet: About 5 cm. Shape: Ovate. Apex: Acute to acuminate. Base: Obtuse. Margin: Serrate. Texture, both surfaces: Smooth, glabrous. Luster: Upper surface: Shiny. Lower surface: Dull. Venation pattern: Pinnate. Color: Young and fully developed foliage, upper surface: 136A; venation, close to 136A. Young and fully developed foliage, lower surface: 138A; venation, close to 138A. Petiole: Length: About 10 cm. Diameter: About 1.5 mm. Texture: Minute thorns, 60A in color. Color: 60A.

Flower description:

*Flower type and habit.*—Flowers terminal, typically one per stem; double flower form. Freely and continuously flowering. Flowers persistent.

*Natural flowering season.*—Flowering continuous throughout the summer in The Netherlands.

*Fragrance.*—Sweet, fresh.

*Flower longevity on the plant.*—About three weeks.

*Flower longevity as a cut flower.*—About 12 to 15 days.

*Flower diameter.*—About 10 cm.

*Flower depth (height).*—About 4.5 cm. Quantity: About 45 per flower in multiple whorls. Length: About 5 cm. Width: About 6 cm. Shape: Cordate. Apex: Rounded; reflexed. Base: Obtuse. Margin: Entire. Texture: Smooth, glabrous. Color: When opening, upper and lower surfaces: 158B. Fully opened, upper and lower surfaces: 157C, outer petals tinged with green, close to 144A; color fading to 155A with subsequent development.

*Sepals.*—Quantity: Five per flower. Shape: Narrowly deltoid with random appendages. Color: Close to 137A.

*Reproductive organs.*—Androecium: Stamen quantity: More than 50 per flower. Anther shape: Oblong, flat. Anther length: About 5 mm. Filament length: About 5 mm. Filament color: 15B. Amount of pollen: Scarce. Pollen color: 17A. Gynoecium: Pistil quantity: More than 50 per flower. Pistil length: About 1 cm. Stigma color: 14C. Style length: About 8 mm. Style color: 13D. Ovary color: 11D.

*Seed/fruit.*—Plants of the new Rose have not been observed to produce fruits and seeds to date.

Disease/pest resistance: Plants of the new Rose has not been observed to be resistant to pathogens and pests common to Roses.

Temperature tolerance: Plants of the new Rose have been observed to tolerate temperatures from 5 to 30° C.

It is claimed:

1. A new and distinct cultivar of Rose plant named 'Roroone', as illustrated and described.

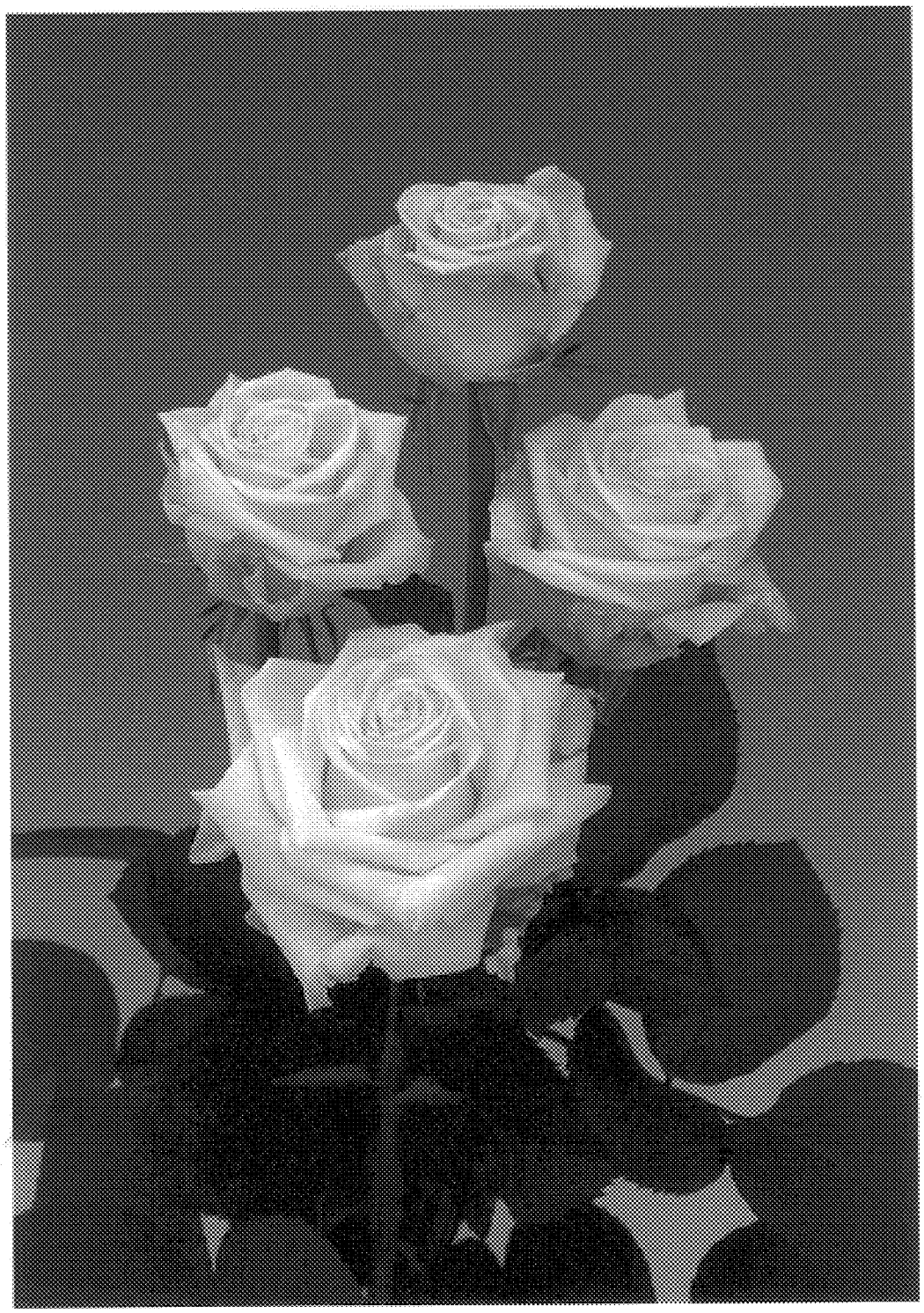

* * * * *